United States Patent
Dow et al.

(10) Patent No.: US 10,120,103 B2
(45) Date of Patent: Nov. 6, 2018

(54) INTELLIGENT/AUTONOMOUS THERMOCLINE MAPPING AND MONITORING FOR MARINE AND FRESHWATER APPLICATIONS

(71) Applicant: INTERNATIONAL BUSINESS MACHINES CORPORATION, Armonk, NY (US)

(72) Inventors: Eli M. Dow, Yorktown Heights, NY (US); Michael Kelly, Albany, NY (US); Harry R. Kolar, Phoenix, AZ (US); Michael L. Passow, Hopewell Junction, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 210 days.

(21) Appl. No.: 14/984,882

(22) Filed: Dec. 30, 2015

(65) Prior Publication Data
US 2017/0192124 A1 Jul. 6, 2017

(51) Int. Cl.
G01K 13/00 (2006.01)
G01V 9/00 (2006.01)
G01N 33/18 (2006.01)

(52) U.S. Cl.
CPC .......... *G01V 9/005* (2013.01); *G01K 13/00* (2013.01); *G01N 33/18* (2013.01)

(58) Field of Classification Search
None
See application file for complete search history.

(56) References Cited

U.S. PATENT DOCUMENTS 8,025,021 B2 * 9/2011 Gosling ............... B63G 8/08
114/312
8,032,314 B2 * 10/2011 Barron ................. G01K 7/42
702/50

(Continued)

FOREIGN PATENT DOCUMENTS

| EP | 431299 A | 6/1991 |
|---|---|---|
| WO | WO2008109187 A3 | 9/2008 |
| WO | WO 2013115732 A2 | 8/2013 |

OTHER PUBLICATIONS

Bentaleb, I., et al "The C 37 alkenone record of seawater temperature during seasonal thermocline stratification." Marine Chemistry 64, No. 4 (1999): 301-313.

*Primary Examiner* — Michael Lebentritt
(74) *Attorney, Agent, or Firm* — F. Chau & Associates, LLC

(57) ABSTRACT

A system for mapping a thermocline in a body of fluid includes a thermocline detection and monitoring module, a persistent data storage module; and a plurality of distributed sensors, including intelligent sensors, connected with the at least one thermocline detection and monitoring module and the persistent data storage module by one or more control-level programming and communication methods. The thermocline detection and monitoring module can monitor the thermocline at sampling intervals to collect and fuse measurement data from the plurality of sensors to capture thermocline changes as events, correlate measurement data and events, store measurement data in the persistent data storage module along with previously acquired measurement data for comparison and tracking, characterize the thermocline as a function of spatial location, depth, and time, create and maintain reports that describe the thermocline characteristics, status, trends, and provide multimodal notifications of events to different users.

20 Claims, 2 Drawing Sheets

(56) References Cited

U.S. PATENT DOCUMENTS

| | | | | |
|---|---|---|---|---|
| 8,152,366 B2* | 4/2012 | Kang | ................ | G01J 5/00 |
| | | | | 374/136 |
| 8,554,377 B2* | 10/2013 | Mathur | ............... | F28D 20/0039 |
| | | | | 165/10 |
| 8,716,880 B2* | 5/2014 | Knowles | ................ | F03B 13/14 |
| | | | | 290/53 |
| 8,894,325 B2* | 11/2014 | Varney | .................... | B63B 35/32 |
| | | | | 405/60 |
| 8,950,191 B2* | 2/2015 | Landis | ................... | F02C 7/143 |
| | | | | 137/15.1 |
| 9,022,692 B2* | 5/2015 | Frazier | ................... | E02D 29/10 |
| | | | | 405/210 |
| 9,023,410 B2* | 5/2015 | Szydlowski | ............. | A23L 2/00 |
| | | | | 426/106 |
| 9,297,919 B2* | 3/2016 | L'Her | ..................... | G01S 11/14 |
| 9,411,063 B2* | 8/2016 | L'Her | ..................... | G01S 11/14 |
| 9,457,900 B1* | 10/2016 | Jones | ..................... | B64C 39/02 |
| 9,563,203 B2* | 2/2017 | Davoodi | ............. | G05D 1/0088 |
| 9,625,592 B2* | 4/2017 | L'Her | ................... | G01V 1/001 |
| 2009/0187369 A1 | 7/2009 | Kang et al. | | |
| 2009/0279381 A1 | 11/2009 | Koopmans et al. | | |
| 2009/0299501 A1 | 12/2009 | Lankinen | | |
| 2013/0077944 A1 | 3/2013 | Tugurlan et al. | | |

* cited by examiner

INTELLIGENT/AUTONOMOUS THERMOCLINE MAPPING AND MONITORING FOR MARINE AND FRESHWATER APPLICATIONS

BACKGROUND

1. Technical Field

Embodiments of the disclosure are directed to an intelligent hardware and software system, possibly embedded and/or distributed, that monitors parameters and events related to changes in the thermal stratification of a water body.

2. Discussion of the Related Art

Thermal stratification occurs in water bodies, both freshwater and marine bodies, as a result of density variations in water as a function of temperature and other variables. The stratification process may be seasonal and can depend on a number of factors including geometry, geography (i.e., latitude, etc.), weather and climate, flows, turbulence, and currents.

Stratification results in three layers of water: (1) an upper (generally) well mixed layer, known as the epilimnion; (2) a transitional zone characterized by rapidly changing temperature, known as the metalimnion; and (3) a dense lower layer, known as the hypolimnion. A thin layer exists within the metalimnion having the greatest water temperature change is known as the thermocline.

Underwater acoustics are affected by stratification, as the velocity of sound changes with temperature, as well as salinity and hydrostatic pressure. In fact, the thermocline can act as a barrier or even a waveguide of sorts for sound. In the marine environment, it is important to understand this phenomenon because it affects underwater communications and military applications such as passive and active SONAR employed for antisubmarine warfare (ASW).

In the case of freshwater lakes, stratification has implications for water quality in that the metalimnion acts as a barrier for oxygen exchange with the mixed upper layer. Reductions in dissolved oxygen can affect patterns of fish behavior as well as change the water chemistry in that nutrients such as nitrogen and phosphorous become more soluble under anoxic conditions and can be released from bottom sediments. These nutrients, which can also affect fish, may later mix with the upper layer and stimulate algal blooms. Algal blooms can further reduce dissolved oxygen levels and also introduce toxins into the water. Other compounds, such as $H_2S$, and metals may also become more soluble and affect water quality.

Given the importance of the thermocline, an automated intelligent measurement/monitoring approach is useful to identify, characterize, and monitor the thermocline both spatially and temporally.

SUMMARY

Exemplary embodiments of the disclosure provide systems and methods for measuring and monitoring the thermocline, wherein sampling of the thermocline can be modified autonomously. Intelligent programming of a vertical profiler can adaptively react to events and/or changing environmental condition, such as high winds or temperatures, and adaptively react to triggers that are computed via a modeling algorithm.

According to an embodiment of the disclosure, there is provided system for mapping a thermocline in a body of fluid that includes at least one thermocline detection and monitoring module (TDMM), a persistent data storage module; and a plurality of distributed sensors, including intelligent sensors, connected with the at least one thermocline detection and monitoring module and the persistent data storage module by one or more control-level programming and communication methods. The at least one thermocline detection and monitoring module can monitor the thermocline at sampling intervals to collect and fuse measurement data from the plurality of sensors to capture thermocline changes as events, correlate measurement data and events, store measurement data in the persistent data storage module along with previously acquired measurement data for comparison and tracking, characterize the thermocline as a function of spatial location, depth, and time, create and maintain reports that describe the thermocline characteristics, status, trends, and provide multimodal notifications of events to different users.

According to a further embodiment of the disclosure, sampling intervals for monitoring the thermocline are autonomously adjusted based on knowledge-based and/or feedback approaches related to changes in thermocline characteristics observed from measurement data, triggered by actual or environmental factors/events or by predictive models or external data.

According to a further embodiment of the disclosure, the at least one thermocline detection and monitoring module is configured to provide trend and predictive analyses of thermocline changes, to monitor predictive models to measure natural physical drivers to thermocline changes, perform dynamic filtering to compensate for environmental parameter changes, and to use machine learning techniques to continuously improve measurement processes.

According to a further embodiment of the disclosure, measurement data includes weather conditions, current information, chemical data, and acoustic data.

According to a further embodiment of the disclosure, the plurality of sensors includes conductivity, temperature, and depth (CTD) sensors, acoustic Doppler current profilers, pinger/depth sounders, sonobuoys, syndicated sources, and multiple heterogeneous data feeds that are supported in real time or asynchronously.

According to a further embodiment of the disclosure, the one or more communications methods include wired, optical fiber, and wireless methods.

According to a further embodiment of the disclosure, at least some of the plurality of sensors incorporate Global Positioning System (GPS) technology to determine location.

According to a further embodiment of the disclosure, the system includes an initialization module that initializes parameters, including sensor parameters, geospatial information, physical characteristics, and data feed characteristics.

According to a further embodiment of the disclosure, the system includes a preprocessing module that examines the measurement data streams for quality to identify data gaps and range inconsistencies.

According to a further embodiment of the disclosure, the system includes a communications module that handles all TDMM communications.

According to a further embodiment of the disclosure, the system includes a sensor interface and control module that provides embedded functionality that controls the plurality of sensors.

According to a further embodiment of the disclosure, the system includes a power management module that provides a constrained power envelope to optimize measurements, analytics, controls, and communications.

According to a further embodiment of the disclosure, the system includes an event handling/alarm services module that sends alerts, classifies events, sets alarm options and priorities, and tags sensor datasets for uncertain data quality.

According to a further embodiment of the disclosure, the system includes an asset management and maintenance management module that provides interfaces to manage a physical platform that hosts the TDMM.

According to another embodiment of the disclosure, there is provided a system for mapping a thermocline in a body of fluid that includes at least one thermocline detection and monitoring module (TDMM) that can monitor the thermocline at sampling intervals to collect and fuse measurement data from a plurality of sensors to capture thermocline changes as events, correlate measurement data and events, store measurement data in the persistent data storage module along with previously acquired measurement data for comparison and tracking, characterize the thermocline as a function of spatial location, depth, and time, create and maintain reports that describe the thermocline characteristics, status, trends, provide multimodal notifications of events to different users, provide trend and predictive analyses of thermocline changes to monitor predictive models to measure natural physical drivers to thermocline changes, perform dynamic filtering to compensate for environmental parameter changes, and to use machine learning techniques to continuously improve measurement processes.

According to a further embodiment of the disclosure, sampling intervals for monitoring the thermocline are autonomously adjusted based on knowledge-based and/or feedback approaches related to changes in thermocline characteristics observed from measurement data, triggered by actual or environmental factors/events or by predictive models or external data.

According to a further embodiment of the disclosure, measurement data includes weather conditions, current information, chemical data, and acoustic data.

According to a further embodiment of the disclosure, the system includes a persistent data storage module; and a plurality of distributed sensors, including intelligent sensors, connected with the at least one thermocline detection and monitoring module and the persistent data storage module by one or more control-level programming and communication methods. The plurality of sensors includes conductivity, temperature, and depth (CTD) sensors, acoustic Doppler current profilers, pinger/depth sounders, sonobuoys, syndicated sources, and multiple heterogeneous data feeds that are supported in real time or asynchronously.

According to a further embodiment of the disclosure, the one or more communications methods include wired, optical fiber, and wireless methods.

According to a further embodiment of the disclosure, at least some of the plurality of sensors incorporate Global Positioning System (GPS) technology to determine location.

DETAILED DESCRIPTION OF EXEMPLARY EMBODIMENTS

Figure 1:
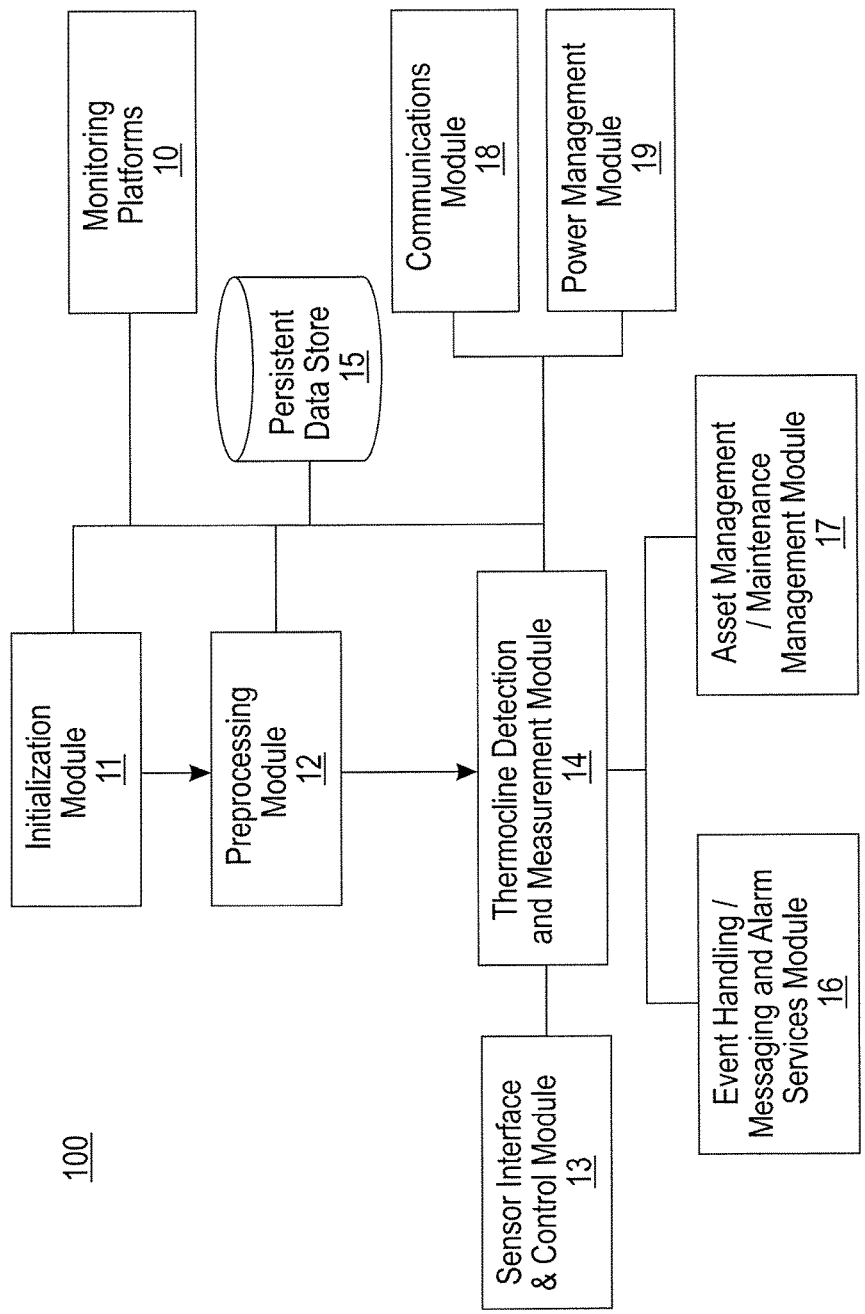
FIG. 1 depicts an exemplary thermocline mapping system 100, according to an embodiment of the disclosure.

Exemplary embodiments of the disclosure as described herein generally include methods for intelligent/autonomous thermocline mapping and monitoring. Accordingly, while the disclosure is susceptible to various modifications and alternative forms, specific embodiments thereof are shown by way of example in the drawings and will herein be described in detail. It should be understood, however, that there is no intent to limit the disclosure to the particular forms disclosed, but on the contrary, the disclosure is to cover all modifications, equivalents, and alternatives falling within the spirit and scope of the disclosure. In addition, it is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Aquatic sensor-based measurement systems generally include one or more monitoring platforms typically deployed via buoys, usually moored, however, they may also be implemented using Lagrangian sensors or even using autonomous underwater vehicles (AUVs), including gliders. Sensor arrays that include mixed technologies are also supported as a common deployment approach. Command and control methods using AUVs launched from offshore or shore-based platforms are also possible.

FIG. 1 depicts an exemplary thermocline mapping system 100, according to an embodiment of the disclosure, and includes an initialization/set up module 11, a preprocessing module 12, a sensor interface and control module 13, the thermocline detection and monitoring module (TDMM) 14, monitoring platforms 10, a persistent data store 15, a communications module 18, a power management module 19, an event handling/alarm services module 16, and an asset management and maintenance management module 17. A thermocline system according to an embodiment of the disclosure can map a thermocline in any body of fluid, and is not restricted to mapping thermoclines in bodies of water.

A TDMM 14 according to an embodiment of the disclosure can perform several functions. A TDMM 14 according to an embodiment can initially identify and characterize a thermocline, including its location and shape, to develop a baseline. According to an embodiment, a thermocline can be represented as a function of spatial location, depth, and time. An approach according to an embodiment involves monitoring over time to detect and characterize the thermocline. Baseline measurements are stored in the persistent data store 15 along with historical data and used for comparison and tracking, to determine how the thermocline position and shape is changing over time. A TDMM 14 according to an embodiment can collect and fuse measurement data from various sources, and correlate data and events. The data includes weather conditions, such as wind velocity, temperature, etc., determined from onboard sensors or from remote stations, chemical data, and current information, received from acoustic Doppler current profilers. Sources include vessels, which can provide acoustic data, such as from pinger/depth sounders and towed arrays; sonobuoys, such as Argo-type buoys, passive arrays, remotely operated underwater vehicles (ROVs), or gliders; syndicated sources, such as a MET matrix or remote sensing feeds; and predictive models that are monitored as they measure natural physical drivers to thermocline changes.

A TDMM 14 according to an embodiment can monitor the thermocline at sampling intervals that are autonomously adjusted based on knowledge-based and/or feedback approaches related to changes in thermocline characteristics that are observed through direct measurements, triggered by actual or environmental factors/events or by predictive models or external data; create and maintain reports that describe the thermocline characteristics, status, trends, along with suitable graphical representations for users or other systems; capture thermocline changes as events and provide multimodal notifications as appropriate to different users; calculate the speed of sound; and provide trend and predictive analyses of thermocline changes.

Any number of algorithmic approaches may be used to do adaptive sampling, including AI machine learning, pattern matching, advanced filtering, feature detection, etc. Examples would include if the system was receiving incoming weather data from remote sensors, such as satellites, offshore monitoring buoys, or predictive weather forecasts that would indicate a significant weather event or change in conditions. High winds and large temperature changes can affect the thermocline. If a vertical profiling system that is continually monitoring the water column, such as a situation where a plurality of sensors have been lowered into the water by a robotic winch assembly, takes measurements every 5 meters, the system would be intelligent enough to know that environmental changes are coming, have sufficient geospatial awareness to understand the context, and in assessing the extent of these changes, determines that the sampling interval should be changed automatically to 1m increments. Alternately, the system could detect changes in the shape of the thermocline or its movement, then decide to sample at a finer scale to better characterize it and perhaps apply predictive approaches to predict the changes. This would be of interest to anti-submarine warfare (ASW) and other applications.

A TDMM 14 according to an embodiment of the disclosure can also perform dynamic filtering to compensate for any environmental parameter changes. For example, consider a wave state, which could affect the vertical measurements, or a large wake that hits a buoy during measurements, such as when a sensor is being lowered on a cable via a robotic winch apparatus. If these events can be detected, bad measurements can be filtered out or compensated. The accuracy of the thermocline characterization is important. So some level of quality is determined, which becomes more critical in domains such as antisubmarine warfare. Quality assessments can be done in many different ways, as is known in the art.

A TDMM 14 according to an embodiment of the disclosure has other capabilities. Machine learning techniques, such as supervised and unsupervised learning techniques, can be utilized to guide and continuously improve measurement processes. In addition, multiple heterogeneous data feeds are supported in real time or asynchronously using a stream analytical processing platform, which may be useful for large instrumentation arrays. A TDMM 14 according to an embodiment can interact with a collection of distributed intelligent sensors attached to other monitoring stations via control-level programming and communications that facilitate a collaborative measurement program to provide an effective means of characterizing the thermocline over a wide area. Notification/alerts are supported via numerous modalities, including high-integrity messaging technologies. Onboard or distributed modeling approaches, such as time series analysis, may also be utilized to provide the trend and predictive analyses of thermocline changes.

The thermocline is responsive to physical changes, such as vertical mixing of a water column due to changes in temperature or density, and it can be influenced by human actions such as large vessels. An example of an action not pertaining to vessels would be a flow into a body of water such as a tributary feed with certain temperatures channeled through a pipe into a lake/reservoir at different depths. Note that in reservoirs, the stratification is actually managed. A TDMM 14 according to an embodiment can detect localized anthropogenic modifications to the thermocline and stratification in the case of large subsurface vessels, and vessel data may be incorporated as a trigger or for analyses.

Monitoring platforms 10 that vertically profile water column characteristics are typically employed to map thermoclines. Conductivity, temperature, and depth (CTD) sensors can be physically lowered via a robotic assembly that is programmed for particular spatial and temporal measurements. Alternative deployment schemes include multiple CTDs that are fixed along the length of moored cables from the surface to the bottom. These measurements can be preprocessed and analyzed by the TDMM 14.

A thermocline mapping system 100 according to an embodiment of the disclosure can be deployed in a topology of co-located sensors and TDMMs, or the sensors may be remote from the TDMM, connected by any number of communications methods. These methods include wired, optical fiber, and wireless (e.g., radio, satellite, etc.) methods. Global positioning system (GPS) technology can be incorporated at each of the TDMMs to capture the location and ensure registration, or the location may simply be preprogrammed into upon initialization using deployment geospatial coordinates.

The initialization/set up module 11 allows a user to initialize a number of parameters which may include sensor parameters, such as type, sensitivity, dynamic and frequency ranges, calibration, sampling frequency, resolution, etc., geospatial information, such as position, water depth, etc., and physical characteristics, such as the types of sensors, sensor location, both relative and absolute, as well as other input data channels from other sensors, such as sea state measurements, including wave height, period, water temperature, salinity, etc., weather inputs, such as wind velocity, temperature, etc., modeling inputs from the predictive models, and other operational measurements. The initialization/set up module 11 can also be used to specify data feed characteristics, such as feed type, format, etc., in the event any ancillary data is used, so that a system according to an embodiment knows what to expect.

The preprocessing module 12 examines the input data streams for quality, using various metrics, to identify data gaps, and range inconsistencies. Irregularities are identified, classified, corrected (if possible), and reported via the event/alarm services module 16. Quality metrics and history can be captured from the persistent data store 15 for event correlation and tracking/monitoring/trend analysis.

The communications module 18 handles all platform communications. It is technology agnostic.

The sensor interface and control module 13 provides embedded control functionality for the sensors and mechanical/robotics for the sampling apparatus, such as winch assemblies, hydroacoustic depth sounders, etc.

The power management module 19 ensures measurements, analytics, controls, and communications are optimized given a constrained power envelope.

The event handling/alarm services module 16 provides the aforementioned services to users, both human and system, to send alerts of appropriate type, such as email, annunciation, SMS, messaging, etc., by name and classes of subscribers. The event handling/alarm services module 16 can classify events, set alarm options and priorities, and tag sensor datasets for uncertain data quality.

The asset management and maintenance management module 17 provides interfaces to an asset management system (AMS) and a maintenance management system (MMS) to manage the physical platform that hosts the TDMM 14. Asset management systems (AMS) and maintenance management systems (MMS) are known in the art and can provide tracking, predictive maintenance, and maintenance (for failures) scheduling and logging. An AMS/MMS can classify failure modes and failure characteristics. There may be particular known failure modes that are relevant. These could include failure during operations, temperature-related failures, failures during power up/down, etc. For asset management, this type of information is helpful as operators of these devices can classify components and systems and their reliability. An AMS/MMS can capture exactly what happens to a component during a failure, such as an open circuit, no power, no response, high/low voltages, resistance, etc. Once component operational characteristics, failure rates, lifetimes, service requirements, etc. are understood, predictive models can be built to drive predictive maintenance and component replacement/replenishment, etc. In line with the above, an AMS/MMS can calculate a risk of component failure or bad data if a service window is exceeded, based on device type, manufacturer, environmental conditions, etc.

As will be appreciated by one skilled in the art, aspects of the present disclosure may be embodied as a system, method or computer program product. Accordingly, aspects of the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present disclosure may take the form of a computer program product embodied in one or more computer readable medium(s) having computer readable program code embodied thereon.

Any combination of one or more computer readable medium(s) may be utilized. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). The computer program code may include components for machine learning, rule-based systems and controls, stream analytical processing, application modules, embedded file systems, including a relational database, a high integrity messaging system, security software, communications software, a Java virtual machine, and power management software.

Aspects of the present disclosure has been described above with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Figure 2:
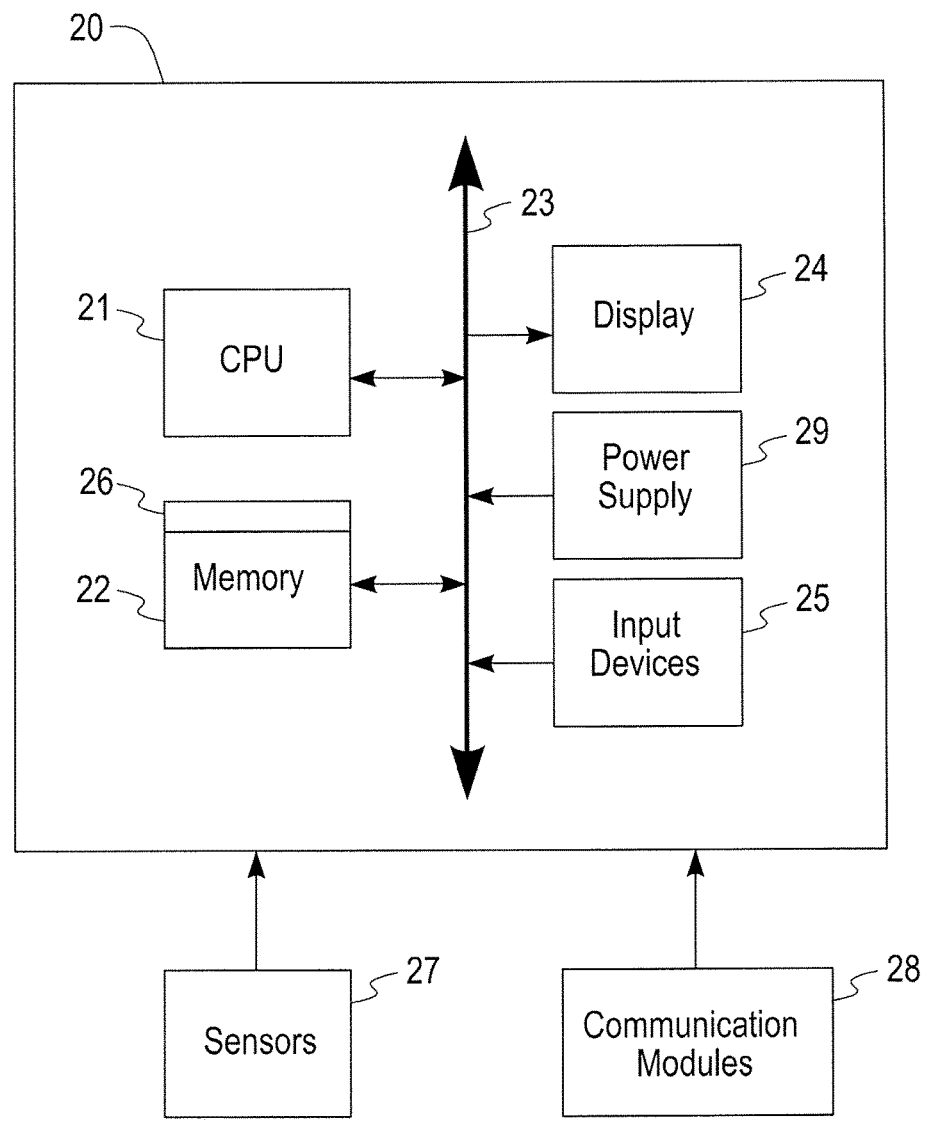
FIG. 2 is a block diagram of an exemplary computer system for implementing a method for intelligent/autonomous thermocline mapping and monitoring according to an embodiment of the disclosure.

FIG. 2 is a block diagram of an exemplary computer system for implementing a method for intelligent/autonomous thermocline mapping and monitoring according to an embodiment of the disclosure. Referring now to FIG. 2, a computer system 20 for implementing the present disclosure can comprise, inter alia, a central processing unit (CPU) 21, a memory 22, an input/output (I/O) interface 23, and a power supply 29. The power can be supplied from a battery, solar panels, windmills, etc. The computer system 20 is generally coupled through the I/O interface 23 to a display 24 and various input devices 25 such as a mouse and a keyboard. The support circuits can include circuits such as cache, power supplies, clock circuits, and a communication bus. The memory 22 can include random access memory (RAM), read only memory (ROM), disk drive, tape drive, etc., or a combinations thereof. The present disclosure can be implemented as a routine 26 that is stored in memory 22 and executed by the CPU 21 to process data signals from the sensors 27, including data for conductivity, temperature, depth, pressure, and current, weather data, and acoustic data from hydrophones, arrays, and fiber optic cables, and communication signals from communication modules 28, such as radio signals and signals from satellites. As such, the computer system 20 is a general purpose computer system that becomes a specific purpose computer system when executing the routine 26 of the present disclosure.

The computer system 20 also includes an operating system and micro instruction code. The various processes and functions described herein can either be part of the micro instruction code or part of the application program (or combination thereof) which is executed via the operating system. In addition, various other peripheral devices can be connected to the computer platform such as an additional data storage device and a printing device.

The flowchart and block diagrams in the figures illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

While the present disclosure has been described in detail with reference to exemplary embodiments, those skilled in the art will appreciate that various modifications and substitutions can be made thereto without departing from the spirit and scope of the disclosure as set forth in the appended claims.

What is claimed is:

1. A system for mapping a thermocline in a body of fluid, comprising:
    at least one thermocline detection and monitoring module (TDMM);
    a persistent data storage module; and
    a plurality of distributed sensors, including intelligent sensors, connected with the at least one thermocline detection and monitoring module and the persistent data storage module by one or more control-level programming and communication methods,
    wherein the at least one thermocline detection and monitoring module
        monitors the thermocline by collecting measurement data from the plurality of sensors at sampling intervals,
        fuses measurement data to capture thermocline changes as events,
        correlates measurement data and events,
        stores measurement data in the persistent data storage module along with previously acquired measurement data for comparison and tracking,
        characterizes the thermocline as a function of spatial location, depth, and time,
        creates and maintains reports that describe the thermocline characteristics, status, trends, and
        provides multimodal notifications of events to different users.

2. The system of claim 1, wherein sampling intervals for monitoring the thermocline are autonomously adjusted based on knowledge-based and/or feedback approaches related to changes in thermocline characteristics observed from measurement data, triggered by actual or environmental factors/events or by predictive models or external data.

3. The system of claim 1, wherein the at least one thermocline detection and monitoring module provides trend and predictive analyses of thermocline changes, to monitor predictive models to measure natural physical drivers to thermocline changes, perform dynamic filtering to compensate for environmental parameter changes, and to use machine learning techniques to continuously improve measurement processes.

4. The system of claim 1, wherein measurement data includes weather conditions, current information, chemical data, and acoustic data.

5. The system of claim 1, wherein the plurality of sensors includes conductivity, temperature, and depth (CTD) sensors, acoustic Doppler current profilers, pinger/depth sounders, sonobuoys, syndicated sources, and multiple heterogeneous data feeds that are supported in real time or asynchronously.

6. The system of claim 1, wherein the one or more communications methods include wired, optical fiber, and wireless methods.

7. The system of claim 1, wherein at least some of the plurality of sensors incorporate Global Positioning System (GPS) technology to determine location.

8. The system of claim 1, further comprising an initialization module that initializes parameters, including sensor parameters, geospatial information, physical characteristics, and data feed characteristics.

9. The system of claim 1, further comprising a preprocessing module that examines the measurement data streams for quality to identify data gaps and range inconsistencies.

10. The system of claim 1, further comprising a communications module that handles all TDMM communications.

11. The system of claim 1, further comprising a sensor interface and control module that provides embedded functionality that controls the plurality of sensors.

12. The system of claim 1, further comprising a power management module that provides a constrained power envelope to optimize measurements, analytics, controls, and communications.

13. The system of claim 1, further comprising an event handling/alarm services module that sends alerts, classifies events, sets alarm options and priorities, and tags sensor datasets for uncertain data quality.

14. The system of claim 1, further comprising an asset management and maintenance management module that provides interfaces to manage a physical platform that hosts the TDMM.

15. A system for mapping a thermocline in a body of fluid, comprising:
    at least one thermocline detection and monitoring module (TDMM) that
        monitors the thermocline by collecting measurement date from the plurality of sensors at sampling intervals,
        fuses measurement data to capture thermocline changes as events,
        correlates measurement data and events, stores measurement data in the persistent data storage module along with previously acquired measurement data for comparison and tracking, characterizes the thermocline as a function of spatial location, depth, and time, creates and maintains reports that describe the thermocline characteristics, status, trends, provides multimodal notifications of events to different users, provides trend and predictive analyses of thermocline changes to monitor predictive models to measure natural physical drivers to thermocline changes, perform dynamic filtering to compensate for environmental parameter changes, and to use machine learning techniques to continuously improve measurement processes.

16. The system of claim 15, wherein sampling intervals for monitoring the thermocline are autonomously adjusted based on knowledge-based and/or feedback approaches related to changes in thermocline characteristics observed from measurement data, triggered by actual or environmental factors/events or by predictive models or external data.

17. The system of claim 15, wherein measurement data includes weather conditions, current information, chemical data, and acoustic data.

18. The system of claim 15, further comprising:

a persistent data storage module, wherein the plurality of distributed sensors include intelligent sensors and are connected with the at least one thermocline detection and monitoring module and the persistent data storage module by one or more control-level programming and communication methods, wherein the plurality of sensors includes conductivity, temperature, and depth (CTD) sensors, acoustic Doppler current profilers, pinger/depth sounders, sonobuoys, syndicated sources, and multiple heterogeneous data feeds that are supported in real time or asynchronously.

19. The system of claim 18, wherein the one or more communications methods include wired, optical fiber, and wireless methods.

20. The system of claim 18, wherein at least some of the plurality of sensors incorporate Global Positioning System (GPS) technology to determine location.

\* \* \* \* \*